(12) United States Patent
Rauh

(10) Patent No.: US 11,154,387 B2
(45) Date of Patent: Oct. 26, 2021

(54) ASSISTANCE SYSTEM FOR DENTAL TREATMENT, IN PARTICULAR BY CHANGING A TOOTH COLOR

(71) Applicant: Vita Zahnfabrik H. Rauter GmbH & Co. KG, Bad Saeckingen (DE)

(72) Inventor: Wolfgang Rauh, Bad Saeckingen (DE)

(73) Assignee: Vita Zahnfabrik H. Rauter GmbH & Co. KG, Bad Säckingen (DE)

( * ) Notice: Subject to any disclaimer, the term of this patent is extended or adjusted under 35 U.S.C. 154(b) by 146 days.

(21) Appl. No.: 16/351,905

(22) Filed: Mar. 13, 2019

(65) Prior Publication Data

US 2020/0246121 A1 Aug. 6, 2020

(30) Foreign Application Priority Data

Jan. 31, 2019 (DE) .................... 10 2019 201 279.5

(51) Int. Cl.
| | | |
|---|---|---|
| *A61C 19/04* | (2006.01) | |
| *A61C 7/00* | (2006.01) | |
| *A61C 19/06* | (2006.01) | |
| *A61Q 11/02* | (2006.01) | |
| A61C 9/00 | (2006.01) | |
| A61C 19/10 | (2006.01) | |

(52) U.S. Cl.
CPC .............. *A61C 19/04* (2013.01); *A61C 7/002* (2013.01); *A61C 19/066* (2013.01); *A61Q 11/02* (2013.01); A61C 9/0053 (2013.01); A61C 19/10 (2013.01)

(58) Field of Classification Search
CPC ....... A61B 1/24; A61B 5/0088; A61B 5/1032; A61C 7/002; A61C 9/0053; A61C 19/04; A61C 19/066; A61C 19/10; A61Q 11/02; G01J 3/508

USPC .......................................................... 433/26
See application file for complete search history.

(56) References Cited

U.S. PATENT DOCUMENTS

| | | | | |
|---|---|---|---|---|
| 5,177,694 | A * | 1/1993 | Graham | ................. A61C 19/10 |
| | | | | 382/165 |
| 6,271,913 | B1 * | 8/2001 | Jung | .................... A61B 5/0088 |
| | | | | 356/402 |
| 9,998,657 | B2 * | 6/2018 | Rauh | ...................... A61C 19/04 |
| 2004/0029068 | A1 * | 2/2004 | Sachdeva | ............. A61C 9/0046 |
| | | | | 433/24 |

(Continued)

FOREIGN PATENT DOCUMENTS

| | | |
|---|---|---|
| DE | 68926120 T2 | 12/1996 |
| DE | 2020008014344 U1 | 4/2010 |

(Continued)

*Primary Examiner* — Matthew M Nelson
(74) *Attorney, Agent, or Firm* — The Webb Law Firm

(57) ABSTRACT

An assistance system for dental treatment, particularly for changing tooth color, is provided herein, including a measuring device for determining tooth data. The data captured is transmitted from the measuring device to a data processing means. The data processing means includes a camera for capturing a tooth mage. Using a selection means, a color change level for the tooth image or the teeth is specified and, thereafter, the tooth image is adapted based on the selected color change level using an adaptation means. Thus, it is possible to show the patient an image of a color change of his teeth caused by the dental treatment in relation to the appearance of his face, so the patient can judge a color change in relation to his or her face.

12 Claims, 2 Drawing Sheets

(56) References Cited

U.S. PATENT DOCUMENTS

| | | | |
|---|---|---|---|
| 2004/0252303 A1* | 12/2004 | Giorgianni | G01J 3/508 |
| | | | 356/402 |
| 2006/0286501 A1* | 12/2006 | Chishti | A61C 7/08 |
| | | | 433/24 |
| 2008/0284902 A1* | 11/2008 | Konno | A61B 5/0013 |
| | | | 348/370 |
| 2009/0168063 A1* | 7/2009 | Kobayashi | G01J 3/02 |
| | | | 356/404 |
| 2012/0134558 A1* | 5/2012 | Sienkiewicz | G06T 7/11 |
| | | | 382/128 |
| 2012/0231421 A1* | 9/2012 | Boerjes | A61C 13/0022 |
| | | | 433/223 |
| 2013/0209954 A1* | 8/2013 | Prakash | A61B 1/042 |
| | | | 433/29 |
| 2014/0200865 A1* | 7/2014 | Lehmann | A61B 6/14 |
| | | | 703/1 |
| 2014/0356798 A1* | 12/2014 | Parker | A61C 7/16 |
| | | | 433/2 |
| 2015/0302581 A1* | 10/2015 | Dursteler | A61C 19/04 |
| | | | 382/128 |
| 2016/0278890 A1* | 9/2016 | Rauh | A61B 1/04 |
| 2018/0116772 A1* | 5/2018 | Korten | A61C 13/0004 |

FOREIGN PATENT DOCUMENTS

| | | |
|---|---|---|
| DE | 102012110491 A1 | 5/2014 |
| DE | 202015002371 U1 | 8/2016 |

\* cited by examiner

ASSISTANCE SYSTEM FOR DENTAL TREATMENT, IN PARTICULAR BY CHANGING A TOOTH COLOR

CROSS-REFERENCE TO RELATED APPLICATION

This application claims priority to German Patent Application No. 10 2019 201 279.5 filed Jan. 31, 2019, the disclosure of which is hereby incorporated by reference in its entirety.

BACKGROUND OF THE INVENTION

The disclosure relates to an assistance system for dental treatment, in particular by changing a tooth color.

For example, when making dental restorations, it is known to first determine the tooth color. The tooth color is typically communicated by indicating a color pattern from a dental color system (e.g. VITA classical A1-D4® or VITA SYSTEM 3D-MASTER®). The determination of the tooth color may be made manually by a dentist or a dental technician. This is done by holding corresponding patterns next to the natural tooth and selecting the pattern best matching the tooth of the patient. The accuracy and reproducibility of such a manual determination of the tooth color are not reliable, since humans perceive colors very differently and the perception also depends on light conditions and the like.

It is also possible to determine the tooth color using an electronic measuring de-vice. Objective and reproducible results are obtained in this manner, which in the ideal case are not compromised by environmental influences. In addition to the tooth color from a dental color system, such devices typically also provide the color coordinates of the measured teeth, e.g. the brightness, the chroma and the shade. The measuring device VITA EASYSHADE® of the company VITA Zahnfabrik is suited for this purpose.

The determination of tooth colors is also feasibly, for example, if a patient wishes a whitening of his teeth, i.e. a so-called bleaching. For this purpose, the current tooth color including the color coordinates of the natural tooth can be determined either manually or electronically using the measuring device VITA EASYSHADE®.

In the next step, it can be determined, in particular by using corresponding pat-terns held next to the natural tooth, which tooth color the patient wishes to have or which tooth color can be achieved by the treatment. This is possible e.g. by using the product VITA Bleachedguide 3D-MASTER® of the company VITA Zahnfabrik developed in particular for application in the context of tooth whitening and including color patterns embodying different brightness levels. A dentist or another person treating the patient can thereby determine by how many (brightness) levels a tooth is to be whitened. The result is the treatment to be applied. In this context, it is difficult, in particular for the patient, to reliably define the desirable tooth color, i.e. by how many levels the teeth shall be whitened. In this respect it has to be taken into consideration that an exaggerated whitening of the teeth is often perceives as unnatural.

It is an object of the disclosure to provide an assistance system for dental treatment, in particular by changing the tooth color. In particular, it is intended that the assistance system of the disclosure gives a patient a good impression of e.g. whitened teeth.

SUMMARY OF THE INVENTION

The object of the disclosure is achieved, according to the disclosure, by an assistance system for dental treatment.

Using the assistance system of the present disclosure for dental treatment in particular by changing the tooth color, it is possible in particular to give the patient an impression of how correspondingly bleached teeth would look like in combination with his complexion and his overall appearance.

For this purpose, the measuring device comprises a measuring device for capturing the tooth data. The measuring device captures the tooth data of the teeth to be treated. In doing so, in particular the color as well as the color coordinates and the brightness level of the tooth are determined. The indications on the device correspond to the results obtained by visual sampling of the teeth using conventional systems such as the VITA classical A1-D4® or VITA SYSTEM 3D-MASTER® or VITA Bleachedguide 3D-MASTER®. It is preferred to capture these data automatically using an electronic measuring device such as the device VITA EASYSHADE®.

The assistance system further comprises a data processing means. This data processing means preferably includes a camera for capturing a tooth image. The camera may also be an external camera whose data are then transmitted to the data processing device. In a particularly preferred embodiment the tooth image not only comprises an image of the teeth alone, but also an image of at least a part of the face so that the appearance of the teeth is visible.

Not only the data of the tooth image captured by the camera are transmitted to the data processing means, but also the tooth data captured with the electronic measuring device. For the transmission of the measured tooth data from the measuring device to the data processing means, the latter preferably comprises a receiving module and the measuring device comprises a transmission module. Although such an automatic transmission by way of a data transmission cable or by wireless transmission is preferred, a manual input of the corresponding data at the data processing means is also possible.

According to the disclosure, the data processing means comprises an integrated allocation module. Using this allocation module, the tooth data are allocated to the tooth image. Preferably, it is specified that the teeth visible in the image include the tooth data determined. In this regard, it is particularly preferred that the allocation of the tooth data to the tooth image is performed such that the appearance of the teeth in the image is specified as corresponding to the measured tooth data. In a preferred embodiment, there is thus no change made to the image data in this step, but it is specified that the teeth visible in that image have the tooth data measured, irrespective of whether the representation is natural or deviates from that due to light conditions or the like. This is of importance, in particular, since the later computational change of the color of the teeth in the image is to generate a realistic result in the captured image.

The assistance system of the present disclosure further comprises a selection means for selecting a degree of color change. The selection means may e.g. be an input mask of the data processing means into which it is inputted that a whitening or a color change by a certain number of levels is to be effected. The means may also be a variably adjustable slide control. In a preferred embodiment, the level of color change is selected as a whitening level. It is preferred that a table containing tooth data is stored in the selection means. From this table, the corresponding data set can be selected to determine a level of color change or a whitening level.

Further, the assistance system of the disclosure comprises an adaptation means. Using the adaptation means, the tooth image is adapted to the selected level of color change or whitening level. In this way it is possible to show the patient an image of his face with correspondingly whitened teeth, wherein it is particularly preferred that the adaptation means only performs a change in the color of the teeth.

In order to allow, in a particularly preferred embodiment, for a change of the color or a whitening of only a tooth region, it is preferred that the data processing means comprises a module for determining a tooth region in the tooth image. This is feasible, since the other regions of the face visible in the picture are not to be changed; rather, the patient is interested in the effects or a changed tooth color on his overall impression. The determination of the tooth region can be made using suitable software for image recognition. The determination of the tooth region is performed e.g. by determining the eye centers or the mean tooth height. Thus, it is possible to define the region in which the teeth in the image are shown. The tooth image captured, which shows at least sections of the face besides the teeth, is thus divided into two regions, i.e. the tooth region and the remaining region of the image which shows at least a part of the face. It is preferred, in particular, that the adaptation means exclusively performs an adaptation of the tooth region.

The disclosure further relates to a method for assisting in a dental treatment, wherein the method is preferably performed using the above assistance system. Tooth data of the teeth to be treated are captured, wherein in particular the tooth color and the color coordinates are captured. Capturing is performed either manually or, as described above with respect to the assistance system, using an electronic measuring device. Further, a tooth image is captured using a camera. The tooth image is either transmitted to a data processing means or is captured directly by the same using an integrated camera. Finally, the tooth data are allocated to the tooth image by an allocation module of the data processing means. Thereafter, a color change level or a whitening level is specified, by which the tooth color is to be changed. Subsequent to that, the tooth image is adapted with reference to the color change level.

The method according to the disclosure is preferably developed in an advantageous manner as described above with respect to the assistance system.

The disclosure will be explained hereunder with reference to a preferred embodiment and to the accompanying drawings.

DESCRIPTION OF THE INVENTION

Figure 1:
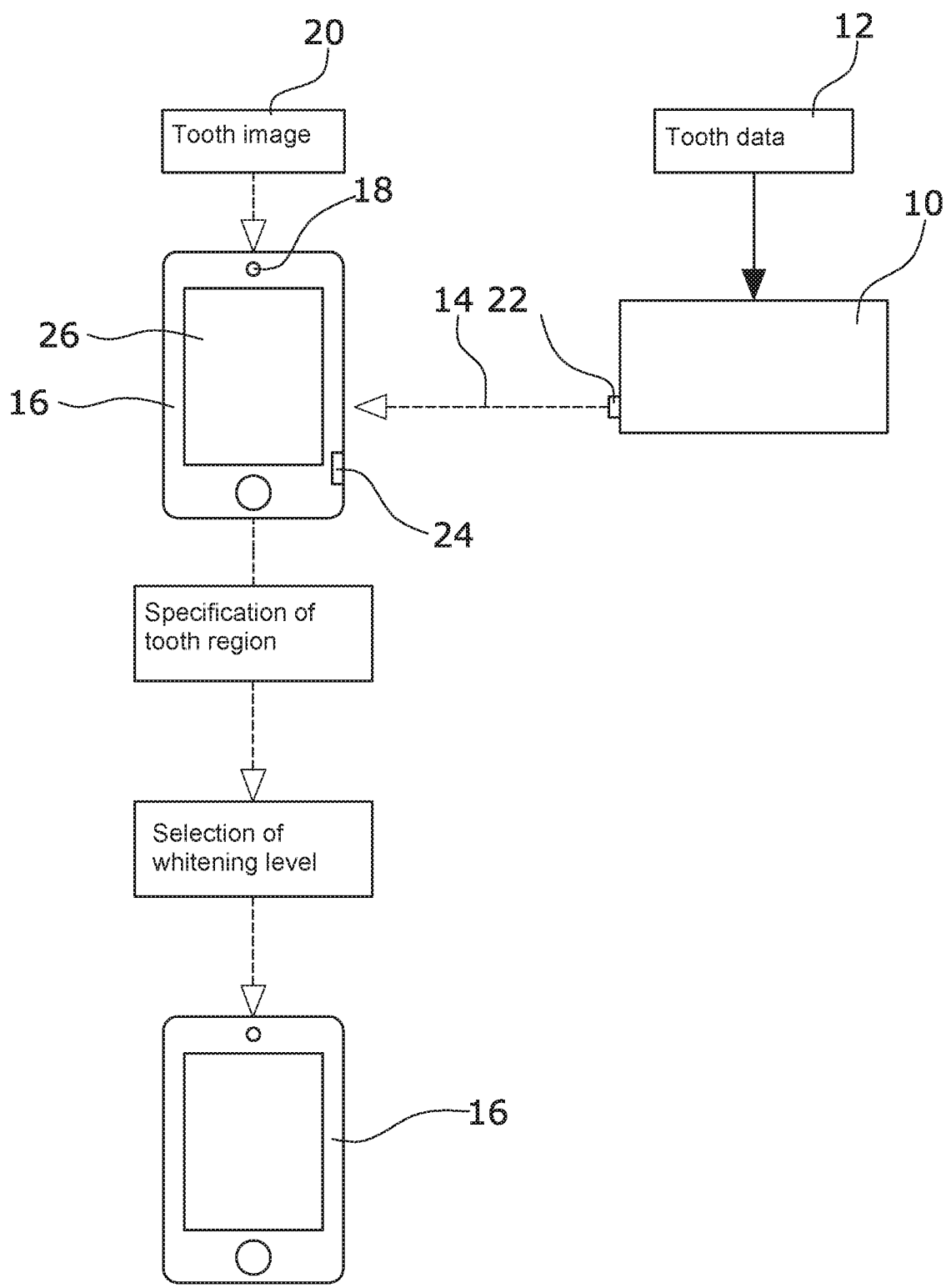
FIG. 1 is a schematic Illustration pf the assistance system.

The assistance system comprises a measuring device 10 for an automatic capturing of tooth data 12. For this purpose, the measuring device 10, which e.g. is the device VITA EASYSHADE®, can be held directly to the teeth. Using a transmission module 22, the detected tooth data 12 are transmitted, as illustrated by an arrow 14, to a data processing means 16, preferably in a wireless manner. The latter may be a smartphone or a tablet. For data capture, the data processing means 16 comprises a receiving module 24.

In the embodiment illustrated, the data processing means 16 comprises an integrated camera 18 for capturing a tooth image 20. The tooth image is then shown on a screen 26 of the data processing means 16, wherein the tooth image preferably shows at least a part of the face.

Figure 2:
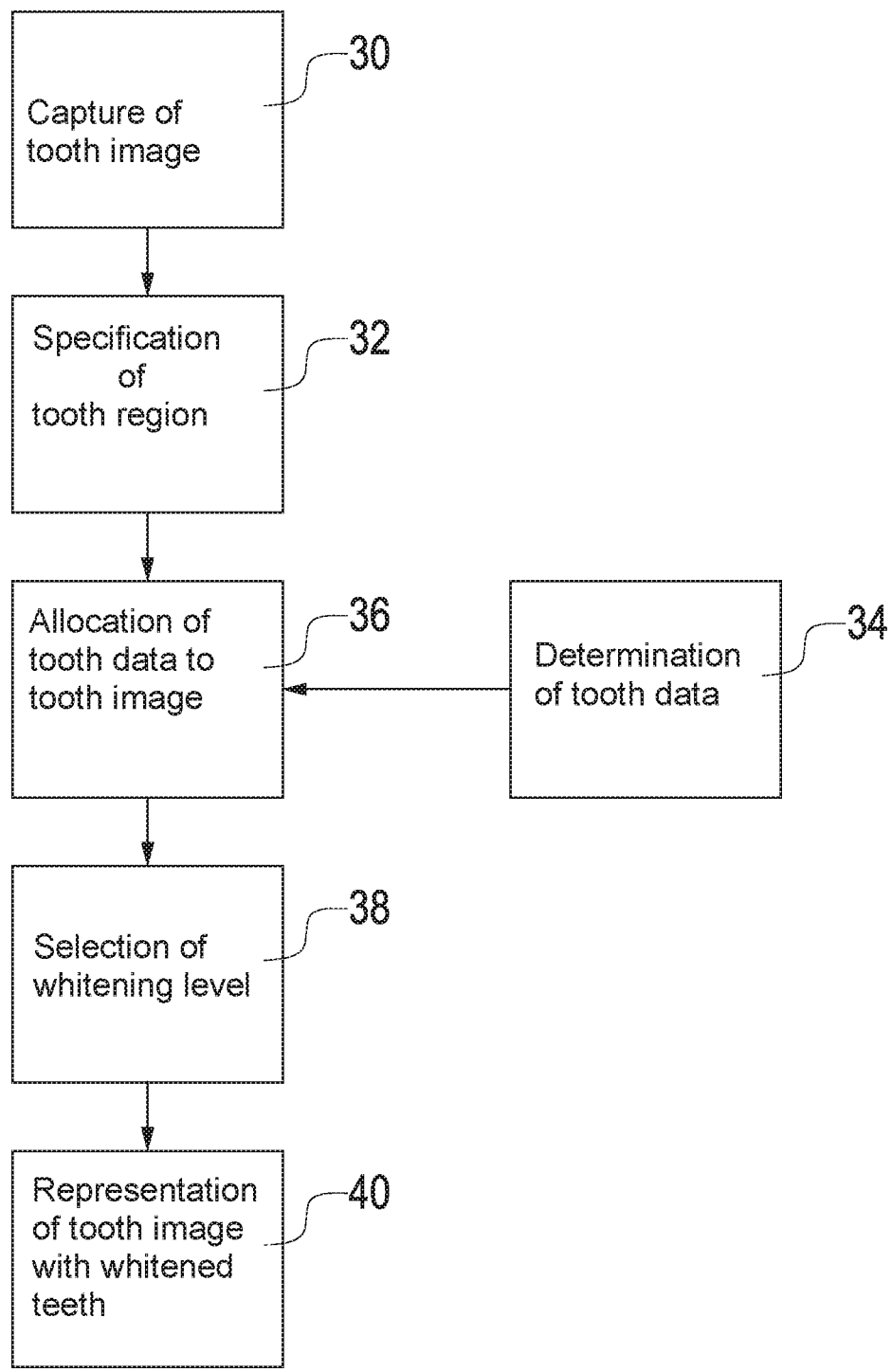
FIG. 2 is a flow diagram illustrating the preferred Functioning of the assistance system.

The preferred use of the assistance system for dental treatment of the disclosure is schematically illustrated in the flow diagram in FIG. 2. First, a tooth image is captured in step 30. Thereafter, in step 32 the tooth region, i.e. the region in the image in which the teeth are shown, is specified using image recognition software.

Using the electronic measuring device 10, tooth data are determined in step 34. In step 36, the tooth data of the natural tooth are then allocated to the current tooth data of the tooth image, i.e. in particular to the tooth region shown in the tooth image. This allocation is made irrespective of the actual representation of the teeth in the tooth image.

In the next step 38, e.g. a whitening level is selected. This may be done using stored tables, the input of a numeric value corresponding to a whitening level, or by means of a variably adjustable control. In step 40, the tooth region is shown in the tooth image with the teeth whitened. In this context, a dynamic change is possible. For example, when a control is provided by which the whitening level can be defined, a change in tooth color can be shown in the image synchronously with the shifting of the control. Thus, it is clearly visible to the Patient how the overall appearance of the face changes by changing the tooth color.

The invention claimed is:

1. An assistance system for dental treatment for changing a tooth color, the system comprising:
   a measuring device configured to directly measure tooth data associated with teeth to be treated, the tooth data including at least one of a tooth color, a tooth coordinate, or any combination thereof;
   at least one data processor; and
   a camera configured to capture a tooth image, wherein the at least one data processor comprises a receiving module, and the measuring device comprises a transmitting module configured to transmit measured tooth data from the measuring device to the at least one data processor, wherein the at least one data processor is configured to:
      allocate received tooth data to a tooth image to determine a correspondence between an appearance of the teeth to be treated in the tooth image and the measured tooth data;
      receive a selection of a level of color change for the teeth to be treated; and
      adapt the tooth image based on the selected level of color change, the measured tooth data, and the determined correspondence between the appearance of the teeth to be treated in the tooth image and the measured tooth data.

2. The assistance system of claim 1, wherein the tooth image comprises at least part of a face.

3. The assistance system of claim 1, wherein the measuring device automatically measures the tooth data.

4. The assistance system of claim 1, wherein the at least one data processor further comprises a module configured to determine a tooth region in the tooth image.

5. The assistance system of claim 4, wherein determining the tooth region comprises a determination of eyes and/or a mean tooth height.

6. The assistance system of claim 1, wherein the adaptation of the tooth image exclusively adapts the tooth region in the tooth image.

7. The assistance system of claim 1, further comprising a table of tooth data is stored in the at least one data processor.

8. A method for assisting in dental treatment for changing a tooth color, the method comprising:
- determining tooth data of teeth to be treated, the tooth data including at least one of a tooth color, a color coordinate, or any combination thereof;
- capturing a tooth image using a camera connected to a data processing unit;
- allocating the tooth data to the tooth image using an allocation module of theft data processing unit to determine a correspondence between an appearance of the teeth to be treated in the tooth image and the measured tooth data;
- specifying a color change level, by which the tooth color is to be changed; and
- adapting the tooth image based on the color change level, the determined tooth data, and the determined correspondence between the appearance of the teeth to be treated in the tooth image and the determined tooth data.

9. The method of claim 8, wherein a measuring device directly determines the tooth data automatically.

10. The method of claim 8, wherein a tooth region in the tooth image is determined using a module of the data processing unit.

11. The method of claim 10, wherein the determination of the tooth region comprises a determination of the eyes and/or the mean tooth height.

12. The method of claim 10, wherein the tooth region in the tooth image is adapted exclusively on the basis of the color change level.

* * * * *

UNITED STATES PATENT AND TRADEMARK OFFICE
CERTIFICATE OF CORRECTION

Page 1 of 1

PATENT NO. : 11,154,387 B2
APPLICATION NO. : 16/351905
DATED : October 26, 2021
INVENTOR(S) : Wolfgang Rauh It is certified that error appears in the above-identified patent and that said Letters Patent is hereby corrected as shown below:

In the Claims

Column 4, Line 63, Claim 6, delete "claim 1," and insert -- claim 4, --

Column 5, Line 9, Claim 8, delete "theft" and insert -- the --

Signed and Sealed this
Eighth Day of February, 2022

Drew Hirshfeld
*Performing the Functions and Duties of the*
*Under Secretary of Commerce for Intellectual Property and*
*Director of the United States Patent and Trademark Office*